United States Patent [19]
Walker
[11] 4,435,179
[45] Mar. 6, 1984

[54] BLOOD BAGS WITH INTERCONNECTING SYSTEM

[75] Inventor: Wolfram H. Walker, Rödermark, Fed. Rep. of Germany
[73] Assignee: Biotest-Serum-Institut GmbH, Frankfurt-Niederrad, Fed. Rep. of Germany

[21] Appl. No.: 319,769
[22] Filed: Nov. 9, 1981
[51] Int. Cl.³ ..................... A61M 5/00
[52] U.S. Cl. ..................... 604/410; 604/244
[58] Field of Search ........... 128/214 R, 214 C, 214 D, 128/214.2, 272, 274; 137/68 R; 251/342; 604/200, 244, 262, 408–410

[56] References Cited

U.S. PATENT DOCUMENTS 2,808,829 10/1957 Butler ..................... 604/408 X
2,894,510 7/1959 Bellamy ..................... 604/408
2,929,378 3/1960 Grosclaude ..................... 128/214 C
3,482,572 12/1969 Grosclaude et al. ........... 128/214 C
4,007,738 2/1977 Yoshino ..................... 128/214 D
4,340,049 7/1982 Munsch ..................... 128/214 R

FOREIGN PATENT DOCUMENTS 49-10156 3/1974 Japan ..................... 137/68
402286 5/1966 Switzerland ..................... 128/214 D

*Primary Examiner*—Dalton L. Truluck
*Attorney, Agent, or Firm*—Sprung, Horn, Kramer & Woods

[57] ABSTRACT

In a blood bag assembly comprising a blood bag and means for connecting the interior of the bag with the interior of a second bag, the improvement wherein said connecting means comprises a coupling composed of a connecting portion, a break-off portion, and a break-off point, the coupling being joined directly at the upper edge of the bag and terminates substantially evenly therewith, the break-off portion will be inside of the bag after it is broken off.

5 Claims, 4 Drawing Figures

BLOOD BAGS WITH INTERCONNECTING SYSTEM

BACKGROUND

Figure 3:
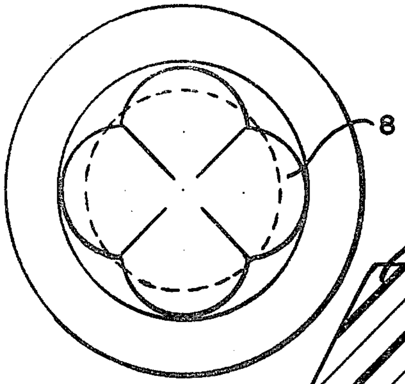

The invention relates to blood bags having an interconnecting system.

Blood bags serve for the taking, storage, preparation and transfusion of blood and blood components. One of the advantages of blood bags over blood bottles of glass is that with multiple blood bag systems blood preparations can be made in a closed, i.e., sterile system. The making of blood preparations is gaining importance in connection with "customized hemotherapy."

Multiple bag systems as available on the market at the present time consist of two or more bag systems in which generally a primary bag contains the blood stabilizer solution and serves for receiving the blood. The secondary or satellite bag, or the satellite bag system which is connected by a system of tubing to the primary bag, serves for the preparation of the blood components such as plasma, factor VIII concentrate, thrombocyte concentrate, etc.

To prevent the solution or blood in the primary bag from passing into the tubing system of the secondary bag system before preparation, the primary bag has a system for interconnection, which, when opened, permits the preparation to pass over from the primary bag to the secondary bag.

For this interconnection system a variety of possibilities exist.

For example, an interconnection system is known which consists of a ball forced into flexible tubing. Free passage is permitted when the ball is squeezed out of the tubing. This system has the disadvantage that, under extreme conditions, such as overpressure, centrifugation, mechanical changes in tubing diameter, etc., the seal is not hermetic.

Systems are furthermore known which utilize clamping means, but they usually have the disadvantage that they are bulky, and that the inserted tube is permanently narrowed or stuck shut before the bag is used, so that when the clamp is opened flow through the tube is constricted.

U.S. Pat. No. 3,110,308 describes a connecting system utilizing a membrane whch is perforated by a cannula-like needle. In this system, the complicated and time-consuming handling is often the subject of complaints.

Lastly, break-off systems are known, in which free passage is made possible by breaking off a plastic piece in a tubing system. Such systems are situated outside of a blood bag in the flexible tubing connecting the primary and secondary bags. This has the disadvantage that often it is impossible to achieve a clean and optimum separation of the blood preparations, after centrifugation for example, and the preparation becomes contaminated. Furthermore, the manufacture and assembly of such systems is complicated and costly.

THE INVENTION

It was therefore the object of the invention to devise an interconnecting system which would offer the advantages of the break-off system, but which at the same time would shut off flush with the blood bag, so that contamination of the secondary bag, after centrifugation for example, is not possible, and the manufacture and operation of the system is very simple and reliable.

This object has been achieved in accordance with the invention by the fact that the interconnection system utilizes a coupling 5, a break-off portion 8, a locus of fracture 9, and, if desired. a collar 6, the coupling 5 being joined directly to the blood bag 1 such that it is situated directly at the upper edge of the bag and terminates substantially even therewith, the break-off portion 8 extending into the bag such that the break-off portion 8 will be inside of the bag after it is broken off.

Figure 1:
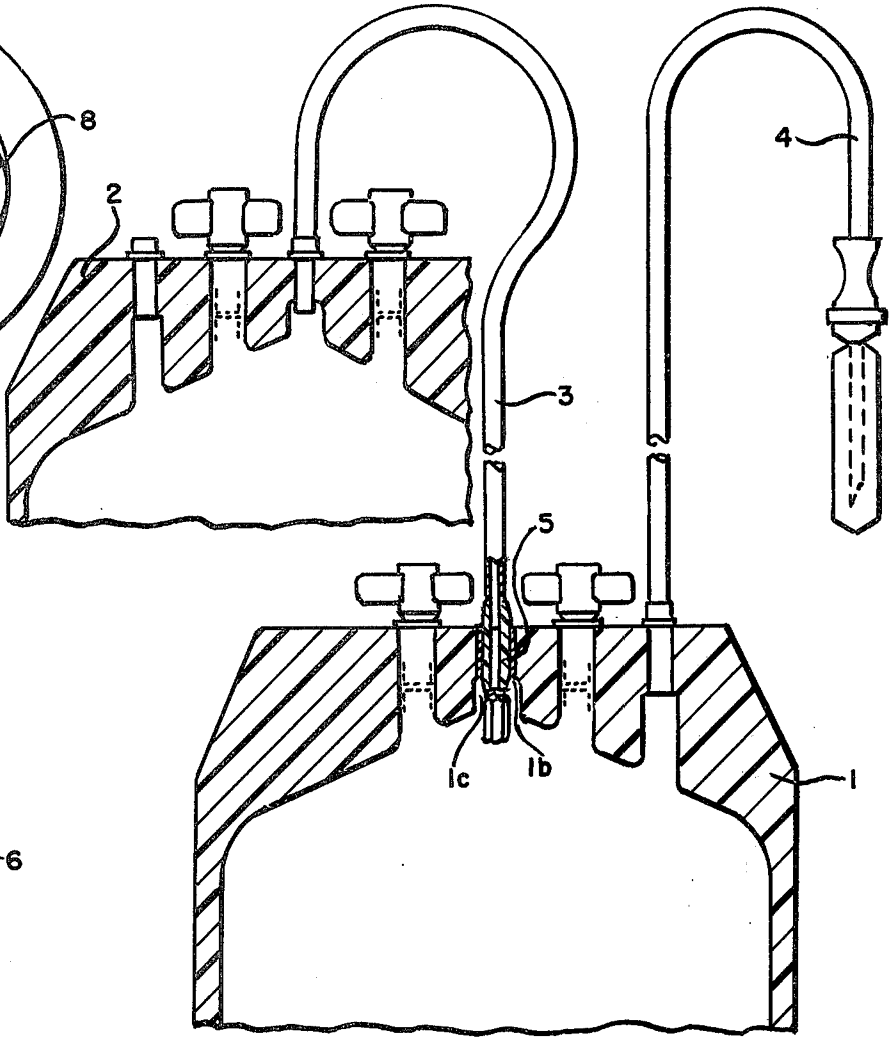
Figure 2:
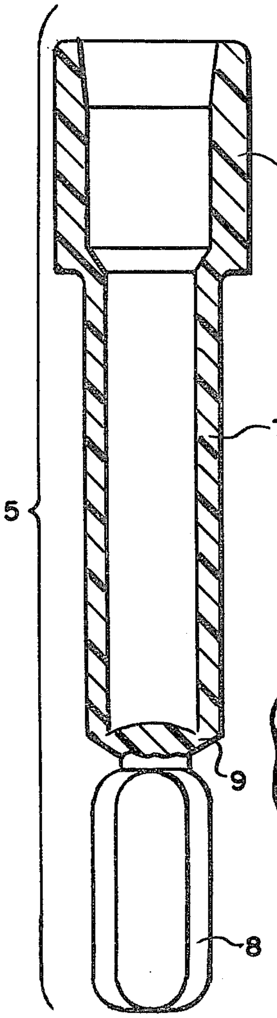
Figure 4:
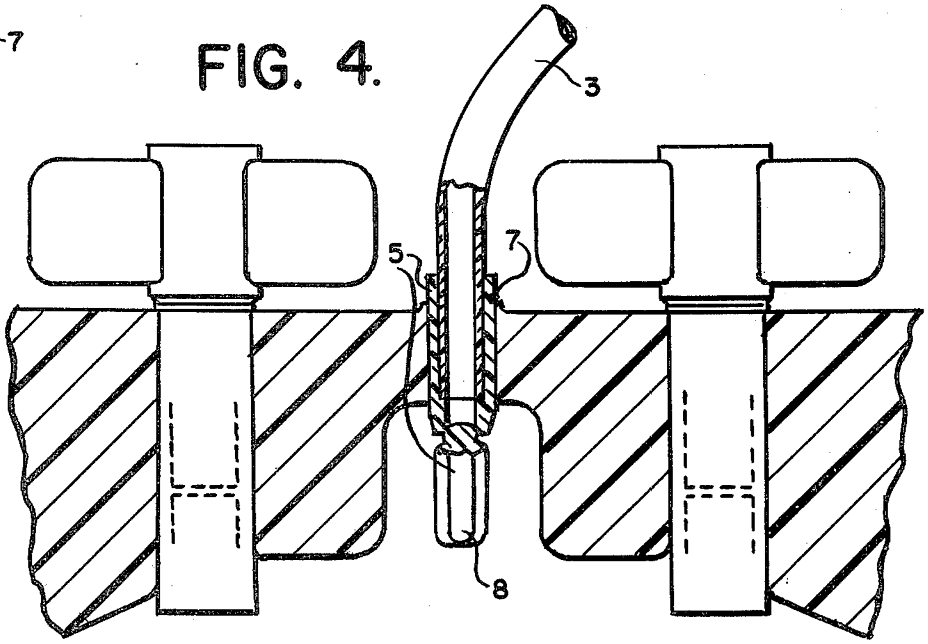
Figure 5:
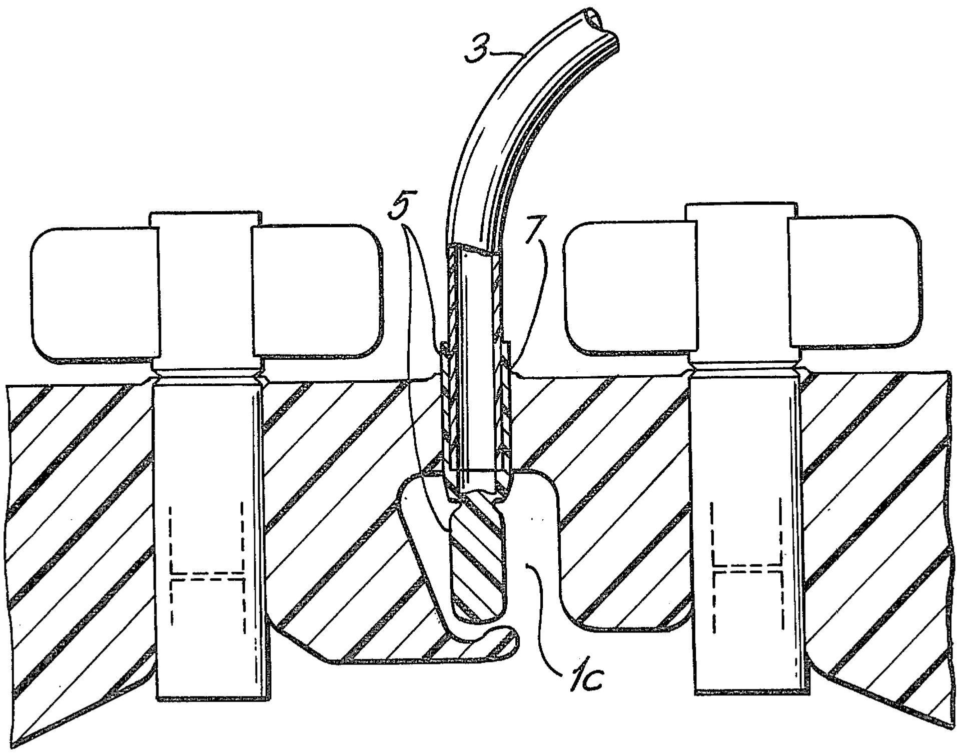

The invention will be further explained with the aid of the drawings, wherein:

FIG. 1 shows a blood bag which contains the interconnection system of the invention and is connected to a second blood bag, FIG. 2 shows the connecting device itself, FIG. 3 shows a cross section through a special embodiment of the break-off piece, FIG. 4 shows an embodiment in which the interconnection system is directly incorporated into the blood bag, without tubing, and FIG. 5 is an enlarged sectional view of another embodiment.

FIG. 1 shows the primary blood bag 1 with the blood taking tube 4, which is connected by a connecting tube 3 with the secondary blood bag 2. The primary blood bag 1 is sealed in a leak-proof manner by the connecting device 5. When the connecting device 5 is opened, the preparation can flow through the connecting tube 3 into the secondary bag 2. In the embodiment shown in FIG. 1, a portion of the connecting device 5 is situated in a recess **1*c*. Also shown is a flexible tube 1*b* which in one embodiment is situated between the blood bag 1 and the connecting device 5**.

FIG. 2 shows a detailed enlargement of the connecting device used as the connecting system. It consists of a collar 6, communicating portion 7, break-off portion 8 and the locus of fracture 9. Upon installation in the blood bag, the collar 6 is attached to the connecting tube 3, the communicating portion 7 is hermetically sealed to the blood bag 1, and the break-off portion 8 is joined with the communicating portion 7 at the locus of fracture 9. The locus of fracture 9 is designed such that, upon breakage, the communicating portion 7 offers free passage corresponding to the open cross-sectional area of the communicating portion 7. If the transfer tube 3 is cemented inside of the collar 6, a free passage through the entire system, corresponding approximately to the free cross sectional area of the connecting tube 3, will form when the break-off portion 8 is broken off.

When the interconnecting device is opened, the break-off portion 8 remains in the primary bag 1. In the embodiment in which it drops freely into the bag, to prevent this piece from blocking the flow during transfusion or during preparation when the preparation is flowing through the tube 3 or any other outlet connection, the break-off portion 8 has a surface of a configuration permitting the fluid to flow past it.

FIG. 3 shows a cross section of a preferred surface configuration of the break-off portion 8, composed of a rosette-like arrangement of four semicircular lobes.

FIG. 4 shows an embodiment in which the connecting device 5, consisting of a communicating portion 7 and a break-off portion 8, is welded directly into the bag. The connecting tubing 3 is in this case cemented into the open end of the interconnection device after the latter has been welded in.

The interconnection device 5 is joined to the blood bag at the communicating portion 7 (FIG. 2), the connecting device 5 being joined by a flexible tube 1*b* of the bag 1 as in FIG. 1, or directly to the bag as in FIG. 4. The tube 3 and the communicating portion 7 of the interconnection device 5 can also be constructed such that the tube 3 is inserted all the way into the communicating portion 7.

The joining of the flexible tube 3 to the interconnection means 5 and to the bag 1 can be accomplished by cementing or welding or other known joining methods, such as ultrasound welding or rotation welding.

The interconnection device 5 is made from a transparent or tinted plastic having optimum characteristics not only for steam sterilization but also for breaking off.

By a gentle transverse pressure on the break-off portion 8, a free through-flow is achieved, and the locus of fracture 9 can be designed such that portion 8 will remain attached to portion 7, but preferably it will snap off completely. Plastics such as hard PVC or Makrolon are appropriate for this purpose. The portion can also consist of material having a specific gravity of less than 1, so that it will float on the blood or blood preparation after being broken off.

The advantage of the interconnection device 5 is that it terminates virtually even with the top edge of the blood bag 1, and thus no contamination of the preparation can occur. As shown in FIG. 1 or 4, the upper edge of the blood bag can also be constructed such that the interconnection device 5 is situated in a recess 1*c* of the bag. This facilitates the breaking-off operation, because blood components in the bag are not stirred up by this operation. The recess 1*c* can also be in the form of a pocket, so that the broken-off piece will not drop freely into the bag but will be retained in the pocket. In this case the surface contouring of the break-off part 8 as illustrated in FIG. 3 for example, is not necessary. FIG. 5 shows an embodiment where the recess 1*c* is constructed as a pocket, the break-off portion 5 being located so that after breaking off it will be retained in the pocket.

It will be understood that the specification and examples are illustrative but not limitative of the present invention and that other embodiments within the spirit and scope of the invention will suggest themselves to those skilled in the art.

I claim:

1. A blood bag assembly comprising at least first and second bags and tubular means connecting the interiors of the bags, the first bag having a sealed flattened edge, the interior of said first bag projecting upwardly into the region of the sealed edge to form a recess, the connecting means including a coupling composed of a connecting portion, a break-off portion and a fracture line located within the recess, the connecting portion being joined directly to said first bag so that it is situated directly at the upper edge of said first bag and terminating substantially evenly therewith, the break-off portion within said recess upon breaking off falling into the inside of the bag and leaving the connecting portion open for free passage of liquid across its full cross-sectioned area.

2. An assembly according to claim 1, wherein the recess is constructed as a pocket, the break-off portion after breaking off being retained in said pocket.

3. An assembly according to claim 1, wherein the break-off portion is formed of a material which has a lower density than blood.

4. An assembly according to claim 1, wherein the cross-section of the break-off portion is a rosette-like cluster of four semi-circles.

5. An assembly according to claim 1, including blood within one of the bags.

* * * * *